United States Patent [19]

Brand

[11] 4,338,346
[45] Jul. 6, 1982

[54] NON-NUTRITIVE SWEETENER

[75] Inventor: Larry M. Brand, West Chester, Ohio

[73] Assignee: The Procter & Gamble Company, Cincinnati, Ohio

[21] Appl. No.: 178,231

[22] Filed: Aug. 14, 1980

Related U.S. Application Data

[63] Continuation of Ser. No. 972,093, Dec. 21, 1978, abandoned.

[51] Int. Cl.$^3$ ............................................. A23L 1/236
[52] U.S. Cl. ...................................... 426/548; 426/3; 426/590; 426/454; 424/49; 424/52; 424/54; 424/56; 424/57; 260/501.11; 562/564
[58] Field of Search .................... 426/3, 548, 540, 454; 424/49, 52, 54, 56, 57; 560/169; 562/564, 565; 260/501.11

[56] References Cited

U.S. PATENT DOCUMENTS 3,971,822 7/1976 Chibata et al. ................. 426/548 X

FOREIGN PATENT DOCUMENTS 1381826 1/1975 United Kingdom .

OTHER PUBLICATIONS

Ferrer Internacional, Chemical Abstracts 87:202129f, 784 (1977).
Marsh et al., J. Pharm. Exptl. Therap., 102, 178–186 (1951).
Mazur et al., JACS, 91(10), 2684–2691 (1969).
Mazur et al., J. Med. Chem., 13(6), 1217–1221 (1970).
Ariyoshi et al., Bull. Chem. Soc. Japan, 47(2), 326–330 (1974).
Miyoshi et al., Bull. Chem. Soc. Japan, 51(5) 1433–1440 (1978).
Brussel et al., Z. Lebenam Unters. Forsch., 159, 339–343 (1975).

*Primary Examiner*—Esther M. Kepplinger
*Attorney, Agent, or Firm*—Michael J. Roth; Eric W. Guttag; Richard C. Witte

[57] ABSTRACT

L-1-hydroxymethyl alkaneamide derivatives of $\alpha$-L-aspartic acid have been prepared and have been discovered to be non-nutritive sweeteners having favorable chemical and physiological properties for use in compositions ingested orally.

8 Claims, No Drawings

NON-NUTRITIVE SWEETENER

This is a continuation, of application Ser. No. 972,093, filed Dec. 21, 1978, now abandoned.

TECHNICAL FIELD

The most widely used natural sweetener for food and similar preparations is sucrose. Sucrose is safe, naturally occurring, and has a high sweetness quality, i.e., a pure, quick onset with no aftertaste or undertaste. One drawback to the use of sucrose as a sweetener is its caloric content. Persons who have diabetes must carefully control their intake of sugar to avoid problems associated with the disease. Persons who have excess weight must use non-nutritive sweeteners since the use of sucrose leads to weight gain rather than weight control or reduction.

A second drawback to sucrose is that it is cariogenic and therefore cannot be used in dentifrices and is undesirable in chewing gums. A third drawback is that sucrose does not have a sufficiently high sweetness intensity for some compositions, e.g. dentifrices. If enough sucrose is used to make the composition sweet, the product becomes tacky and hygroscopic. Additionally, for the amount of sweetness delivered, sucrose is expensive.

It can be appreciated that the search continues for compounds which have high sweetness intensity and quality, are non-nutritive, and are safe for oral consumption.

Numerous compounds have been discovered which are non-nutritive sweeteners. However, most have drawbacks of one sort or another. Sodium cyclamate has been banned for oral use because it may be carcinogenic or mutagenic. Saccharin is also being questioned as a possible carcinogen; additionally, saccharin has a bitter aftertaste. Neohesperidine dihydrochalcone has 900 times the sweetness of sucrose; however, the sweetness is slow to develop and there is a licorice-like aftertaste. Aspartame ®, a dipeptide, has a high quality sweetness of approximately 150 times sucrose, but hydrolyzes in aqueous solution to its non-sweet component amino acids. Other aspartic acid derivatives are sweet but hydrolyze in the gastrointestinal tract to release potent vasopressors.

Non-nutritive sweeteners have been known for almost one hundred years (saccharin, 1879) and theories have been proposed to account for the perception of sweetness and the chemical structures that produce that perception. Yet, there seems to be no common molecular property which can be used to predict either the level or, especially, the quality of sweetness. Ingenious models have been proposed to explain the sweetness of known compounds, but not all compounds fitting the models are sweet and the theories cannot be used to predict or construct new sweeteners. The prediction of the quality of sweetness, as well as the intensity of sweetness, appears to remain a complete mystery.

The compounds of the present invention, L-1-hydroxymethyl alkaneamide derivatives of α-L-aspartic acid, have not previously been prepared. It has now been discovered that, surprisingly, the compounds are sweet and are physiologically safe for oral use in sweetening amounts, even though similar alkaneamide derivatives have drug activity. The compounds of the present invention do not have a labile ester linkage and so are much more stable in aqueous solution than dipeptides such as L-aspartyl-L-phenylalanine methyl ester. Additionally, the preferred compound disclosed herein also has a sweetness quality equivalent to sucrose while having a sweetness intensity some 50 times greater than sucrose.

BACKGROUND ART

Investigations into derivatives of aspartic acid as non-nutritive sweeteners stem from the accidental discovery that L-aspartyl-L-phenylalanine methyl ester (Aspartame ®) is sweet, 100–150 times sucrose, and free of unpleasant aftertaste. R. H. Mazur, J. M. Schlatter, and A. H. Goldkamp, JACS, 91, 2684 (1969). The authors disclosed that the L-aspartic acid portion of the molecule is critical for sweetness, but that considerable modification of the phenylalanine portion could be tolerated.

Subsequent work investigated the structural relationships of aspartic acid amides as regards sweetness. R. H. Mazur, A. H. Goldkamp, P. A. James, and J. M. Schlatter, J. Med. Chem. 13, 12–17 (1970). The authors' investigations revealed that the structural requirements for good sweetness in derivatives of L-aspartic acid are quite specific, as is revealed by tests of the L-aspartate amides:

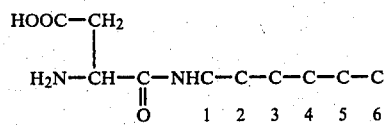

4-methylpentylamide—tasteless
1-ethylbutylamide—bitter
hexylamide—sweet, 1–2 X sucrose
heptylamide—sweet, 1–2 X sucrose
1-methylbutylamide—tasteless
1-methylpentylamide—sweet, 30 X sucrose
1-methylhexylamide—sweet, 20–50 X sucrose
1-methylheptylamide—sweet, 10 X sucrose
1,3-dimethylbutylamide—bitter
1,3-dimethylpentylamide—sweet, 1–2 X sucrose
1,4-dimethylpentylamide—sweet, 50–100 X sucrose All the sweet isomers were found to be L—L. The 1-methylhexylamide was about 20–50 times the sweetness of sucrose and the 1,4-dimethylpentylamide was about 50–100 times the sweetness of sucrose.

British Pat. No. 1,381,826, Neely, January 29, 1975, claims the use of L-aspartyl-L-1,4-dimethylpentylamide in oral compositions as a sweetener.

Y. Ariyoshi, N. Yasuda, K. Yamatani, Bull. Chem. Soc. Japan, 47, 326 (1974) describe investigations into the sweetness of hydroxy-substituted derivatives of L-aspartyl dipeptides. They report that α-L-aspartyl-L-1-methyl-2-phenethylamine (aspartyl amphetamine) was 50 times as sweet as sucrose; however, L-aspartyl-L-1-hydroxymethyl-2-methyl-2-phenethylamine was only 1 to 2 times as sweet as sugar. The authors report that with an L,L configuration, hydroxyl substitution always decreased potency of sweetness, while with L,D configurations, hydroxy substitution sometimes increased potency and sometimes decreased it. Methyl substitution at the 2 or 3 position produced bitter tasting compounds.

1-(1-hydroxyethyl) derivatives of α-L-aspartic acid have no sweetness. L. B. P. Brusse, H. C. Peer, A. van der Heijden, Z. Lebensm. Unters. Forsch., 159, 339 (1975).

M. Miyoshi, K. Nunami, H. Sugano, T. Fujii, Bull. Chem. Soc. Japan, 51, 1433 (1978) disclose L-aspartyl dipeptides of the formula:

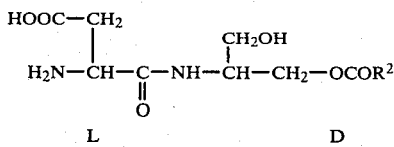

as being sweet. The authors state that none of the O-acyl-L-aspartylamino-L-alkanols synthesized were sweet and that the C-terminal amino acid must be the D form to exhibit sweetness.

Belgian Pat. No. 851,368, Ferrer, May 5, 1977 discloses the compound α-L-aspartyl-1,5-dimethyl-5-hydroxyhexylamide (claimed as the L-aspartate of 6-amino-2-methyl-2-heptanol) for use in the treatment of cardiac and pulmonary insufficiency.

In the gastrointestinal tract, L-aspartyl alkaneamides and L-aspartyl-1-hydroxymethyl alkaneamides are hydrolyzed to aspartic acid and the corresponding amine by aminopeptidase enzymes. E. F. Marsh, D. A. Herring, J. Pharm. Exp. Therapy, 102–178 (1951) describe a study of the comparative pharmacology of hydroxyl and methyl derivatives of 1,5-dimethylhexylamine (named as 6-methyl-2-heptylamine by the authors). These compounds would be produced by the hydrolysis of the L-aspartyl dimethylhexylamide. The data show the amine compound to have vasopressor and myocardial stimulant activity. This activity is shown to be lessened somewhat by 5-hydroxyl or 2- or 3-methyl substitution. 1,5-dimethylhexylamine has been sold commercially as a vasoconstrictor (Octodrine); 1,3-dimethyl pentylamine has been sold as a vasoconstrictor (Forthane); 1,5-dimethylaminohexan-5-ol hydrochloride has been sold as a cardiac stimulant and coronary vasodilator (Heptanol).

DISCLOSURE OF THE INVENTION

The present invention encompasses compounds of the formula:

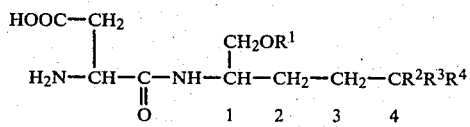

wherein said compound is in the L, L form; and wherein $R^1 = H$,

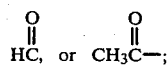

$R^2 = H$ or $CH_3$; $R^3 = H$ or $CH_3$; and $R^4 = CH_3$, $C_2H_5$, i—$C_3H_7$, or t—$C_4H_9$, except that where $R^4$ is i—$C_3H_7$ or t—$C_4H_9$, $R^2$ and $R^3$ are H; and toxicologically acceptable salts thereof.

The present invention also encompasses compositions of matter comprising an ingestible carrier, i.e., food, beverage, drug, mouthwash, dentifrice, or other compositions designed for oral use, containing an effective sweetening amount of a compound having formula I, above.

The present invention arises from the discovery that hydroxymethyl substitution at the 1-position in the L-alkaneamide moiety of L-aspartyl amides of formula I, above, not only reduces the pharmacological activity of the amine portion of the amide (and therefore of the amide itself) but also produces intensely sweet amides.

The preferred sweetener compound herein is N-(α-L-aspartyl)-L-1-hydroxymethyl-4-methylpentylamide, of the formula:

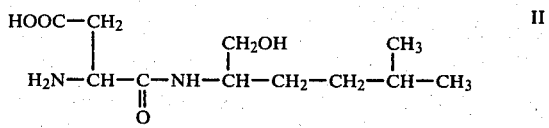

The preferred sweetener compound II is approximately 50 times as sweet as sucrose and has a sweetness quality approximately equal to sucrose. Additionally, compound II is sweet in both aqueous solution and granular form. Compound II is particularly useful as a sugar substitute for diabetics or weight conscious persons.

Non-nutritive sweeteners which are amide derivatives of L-aspartic acid are most commonly used in the form of salts. Salts are preferred as the salts dissolve rapidly and also provide a more rapid onset of sweetness than the amide compound per se. "Toxicologically acceptable salts" as used herein refers to salts of the instant compounds which are physiologically acceptable for ingestion. Typical toxicologically acceptable salts of the present sweeteners are sodium, potassium, calcium, and ammonium salts as well as hydrohalide, and especially hydrochloride, addition salts.

The 1-hydroxymethyl substituent group present in compounds of formula I can be in the unsubstituted alcohol form or can be esterified with lower alkyl carboxylic acids, especially formic or acetic acid. Although the ester itself may not be sufficiently sweet for all purposes, once the esterified-1-hydroxymethyl amide is placed in an aqueous environment, ester hydrolysis will begin to occur to produce the preferred, sweet aspartyl-1-hydroxymethyl substituted amide.

The L-aspartyl-L-1-hydroxymethyl alkaneamides of the invention are useful for sweetening a variety of food products such as fruits, vegetables, juices, meat products such as ham or bacon, sweetened milk products, egg products, salad dressings, ice creams and sherbets, gelatins, icings, syrups, cake mixes and frostings, as well as for sweetening beverages such as carbonated soft drinks and wines. The compounds of the invention can also be used to sweeten dentifrices, mouthwashes, and chewing gums, as well as drugs such as liquid cough remedies.

The instant sweetening agents are stable substances and can be used in a variety of physical forms, e.g., as powders, tablets, syrups, pastes, solutions, etc. Liquid or solid carriers such as water, glycerol, starch, sorbitol, salt, citric acid and other suitable nontoxic substances can also be used as carriers. The sweetening agents can readily be used in pharmaceutical compositions to impart a sweet taste.

The sweetening agents are used in effective sweetening amounts. By "effective sweetening amounts" as used herein is meant sufficient sweetening agent to provide a sweet taste of the desired intensity for the orally ingested composition. The amount added will generally depend upon commercial needs as well as individual sweetness sensitivity.

Representative sweetener compounds of formula I include N-α-L-aspartyl L-amide derivatives wherein the L-amide moiety is:

1-hydroxymethyl-4,4-dimethylpentylamide
1-hydroxymethyl-5-methylhexylamide
1-hydroxymethylhexylamide
1-hydroxymethyl-4-methylhexylamide
1-hydroxymethyl-4,4-dimethylhexylamide
1-hydroxymethylpentylamide
1-hydroxymethyl-5,5-dimethylhexylamide Some of the above compounds, although sweet, are not as preferred as the L-1-hydroxymethyl-4-methylpentylamide by reason of solubility or sweetness quality. For example, the aspartyl L-1-hydroxymethyl-5-methylhexylamide is somewhat slow to dissolve. The aspartyl L-1-hydroxymethyl-4,4-dimethylpentylamide, is sweet in both granular form and in aqueous solution, but has somewhat of a melon-like undertaste.

The synthesis of the compounds of formula I is a multi-step process. In general, the compounds can be made through either of two generalized synthetic procedures, (A and B, below) both involving an enzymatic optical isomer resolution step and both of which, although time consuming, involve only standard organic synthesis techniques.

Procedure A

Step 1—Using standard techniques, the appropriate D,L-2 aminoalkanoic acid is prepared by the reaction of diethylacetamidomalonate with sodium ethoxide in anhydrous ethanol followed by the addition of the appropriate alkylhalide. The compound thus formed is deacetylated, and the sodium salt form, by refluxing with an alkali metal hydroxide, and decarboxylated by acidification. Purification yields the D,L-2-aminoalkanoic acid racemic mixture.

Step 2—The D,L amino alkanoic acid racemate from Step 1 is enzymatically resolved. After N-acetylation of the D,L- amino alkanoic acid in glacial acetic acid with acetic anhydride, the N-acetyl-D,L-acid is contacted with Acylase I. Acylase I is a commercially available compound, N-acylamino acid aminohydrolase, obtained from hog kidneys. After reaction with the aminohydrolase, acidification with acetic acid yields the desired L-2-amino alkanoic acid L-2-amino-5-methylhexanoic acid, for example, upon evaporation of the filtrate.

Step 3—L-2-aminoalkanol is prepared by lithium aluminum hydride reduction of the methyl ester hydrochloride of the L-aminoalkanoic acid from Step 3.

Step 4—The sweetening agent of formula I is produced from the reaction in an anhydrous aprotic solvent of commercially available N-trifluoroacetyl-L-aspartic acid with the L-1-hydroxymethyl alkaneamine.

An alternate procedure is as follows:

Procedure B

Step 1—The appropriate α-bromoalkanoic acid, prepared by reaction with bromine and $PCl_3$, is added to a solution of ammonium carbonate and ammonium hydroxide. After precipitation, filtration, and recrystallization, the D,L-2-amino alkanoic acid is obtained.

Step 2—The racemic alkanoic acid mixture is resolved, as in Step 2 of Procedure A.

Step 3—The L-1-hydroxymethyl alkaneamine is produced by reaction of the L-aminoalkanoic acid with a diborane/tetrahydrofuran solvent system, followed by acid hydrolysis.

Step 4—The sweetening agent of formula I is recovered after reaction of N-carbobenzoxy-L-aspartic acid β-benzyl ester with the L-1-hydroxyalkaneamine in methylene chloride in the presence of dicyclohexylcarbodiimide, followed by dissolution of the N-carbobenzoxy-α-L-aspartyl L-1-hydroxy methyl alkaneamide so produced in acetic acid to which Pd on charcoal is added. After hydrogenation, the sweetener of formula I is recovered after purification by high pressure liquid chromatagraphy (HPLC) and recrystallization.

The various solvents, derivatives of aspartic acid ane techniques used in Procedures A and B are well known and are in the synthetic chemist's repertoire.

BEST MODE

The following illustrates the complete synthesis of the preferred sweetener compound of this invention (formula II). The procedure is readily modified to provide the various salts, esters, and the like, disclosed hereinabove.

Synthesis of N-(α-L-Aspartyl)-L-1-hydroxymethyl-4-methylpentylamide according to General Procedure A.

Step 1: Synthesis of D,L-2-amino-5-methyl hexanoic acid.

3.80 g of sodium was added to 300 ml anhydrous ethanol and allowed to react completely. To this was added 39.6 g diethylacetamidomalonate (under an $N_2$ stream); the resulting solution was stirred for 45 minutes. 3-methyl-1-bromobutane was then added dropwise, with heating, over the next 20 minutes. The mixture was refluxed for 20 hours. The solution was then filtered to remove salts; the resulting filtrates were evaporated to yield 48.97 g yellow solid. This material was taken up in 100 ml ether and applied to a 450 g silica gel column. Elution with 2700 ml ether afforded 28.0 g of solid after evaporation. This material was refluxed for 20 hours with 150 ml of 20% NaOH (to remove the N-acetyl group). The resulting solution was chilled in an ice-water bath and acidified through slow addition of 150 ml conc. HCl. This solution was then refluxed for 2 hours, cooled to room temperature, and adjusted to pH 6 with 25% NaOH. After standing at room temperature for 2 hours, the solids which precipitated were filtered, and dried in vacuo to yield 10.4 g product (80% yield), D,L-2-amino-5-methylhexanoic acid.

Step 2: Synthesis of L-2-amino-5-methylhexanoic acid (resolution of racemic amino acid).

20.0 g of DL-2-amino-5-methylhexanoic acid and 150 ml glacial acetic acid were combined in a 250 ml flask and the suspension stirred at 57° C. To this mixture was added dropwise 30.9 g acetic anhydride over a period of 20 minutes at 47° C. The resulting solution was then stirred at room temperature for 2 hours, after which solvents were removed in vacuo to yield a white semisolid. This material was suspended in 20 ml $H_2O$ and re-dried three times to yield a white solid, which was recrystallized from ether/acetone to yield 20.7 g of the product, N-acetyl-DL-2-amino-5-methylhexanoic acid.

18 g of N-acetyl-D,L-2-amino-5-methylhexanoic acid material was taken up in 700 ml $H_2O$, and concentrated. $NH_4OH$ was added to reach pH 7.2. The solution was heated to 36° C. and 11.0 mg Acylase I was added. After stirring for 18 hours, an additional 5 mg Acylase I was added and the solution stirred an additional 24 hours. The solution was then acidified with 18.0 ml acetic acid and filtered. Evaporation of the filtrate yielded the product, a white solid, L-2-amino-5-methylhexanoic acid, (5.8 g, 83% yield).

Step 3: Synthesis of L-2-amino-5-methylhexanol

L-2-amino-5-methylheptanoic acid (5.8 g) was suspended in 250 ml anhydrous methanol and anhydrous HCl gas bubbled into the stirred mixture in an ice-water bath to achieve saturation. The reaction was stirred at 10° C. for 1 hour and at room temperature for 18 hours further. Evaporation of the solvent yielded 8.02 g of L-2-amino-5-methylhexanoic acid methyl ester.HCl (white solid).

Under $N_2$ atmosphere, 2.3 g lithium aluminum hydride and 300 ml anhydrous tetrahydrofuran were placed in a 500 ml flask and the amino methylhexanoic acid methyl ester.HCl salt (8.0 g) was added in small portions over ½ hour. The mixture was stirred at room temperature for 1 hour. 25 ml ethyl acetate was added and the mixture stirred an additional ½ hour. 160 ml $H_2O$ was added dropwise, and the solution extracted with 1 liter ether and 500 ml ether. The combined ether fractions were washed with 3×100 ml portions of saturated NaCl, and dried over $MgSO_4$. After evaporation of the solvent, 4.9 g yellow oil, L-2-amino-5-methylhexanol, was obtained (91% yield).

Step 4: Synthesis of N-(α-L-Aspartyl-L-1-hydroxymethyl-4-methylpentylamide

Trifluoracetic anhydride (149 g) was placed in a 500 ml flask and chilled to −78° C. L-aspartic acid (37.8 g) was then added in small portions over 5 minutes and the resulting slurry stirred for 10 minutes while chilled to −78° C. After removal of the cooling bath, the mixture was stirred for an additional 2 hours. After the vigorous reaction subsided, the solution was refluxed for one hour, allowed to cool, and poured into 300 ml hexane, yielding a white solid. After washing successively with 200 ml hexane and 400 ml ether, the material was dried in vacuo, yielding 57.2 g N-trifluoroacetyl-L-aspartic acid anhydride (96% yield).

1.0 g of this material was added to 20 ml anhydrous tetrahydrofuran in a sealed flask and 0.62 g of L-2-amino-5-methylhexan-1-ol added in small portions under $N_2$ atmosphere. After 3 days, the solvent was removed, yielding N-(trifluoroacetyl)-L-aspartyl-DL-2-amino-5-methylhexanol (2.0 g including some solvent). This material was combined in a flask with 15 ml of 7.4 N $NH_4OH$ and heated to 80°–85° C. for 7 minutes. The mixture was cooled, and the solvents removed in vacuo yielding the crude product. After recrystallization of this material from butanol/water, the yield was 254 mg of N-(α-L-aspartyl)-L-1-hydroxymethyl-4-methylpentylamide (Mp. 216°–218° C.).

The following is an alternative method for synthesizing N-(α-L-aspartyl)-L-1-hydroxymethyl-4-methylpentylamide according to general Procedure B.

Step 1: Synthesis of DL-2-amino-5-methyl hexanoic acid

To a 250 ml flask was added, successively, 76 g 5-methylhexanoic acid, 30 ml $Br_2$ and 2.0 ml $PCl_3$. The solution was warmed to 65°–75° C. for 4 hours, after which 2 ml additional $Br_2$ was added. The reaction was then warmed to 100°–105° C. for an additional 2 hours. The solution was then cooled to room temperature and stirred for 18 hours. Excess $Br_2$ and HBr were removed by heating to 80° C. under light vacuum (20 minutes). Distillation of the resulting solution yielded 93.2 g product (115° C., 0.4 mm). (76% yield).

The α-bromo acid (93 g) was then added dropwise to a warmed (45° C.) solution containing 196 g ammonium carbonate, 70 ml $H_2O$ and 200 ml concentrated ammonium hydroxide. This solution was stirred for 22 hours at 45° C. and the material that precipitated was filtered and recrystallized from 1700 ml $MeOH/H_2O$ (75/25) to yield 21.6 g D,L-2-amino-5-methyl hexanoic acid (34% yield from α-bromo acid).

Step 2: Synthesis of L-2-amino-5-methylhexanoic acid (resolution of racemic amino acid)

20.0 g of D,L-2-amino-5-methylhexanoic acid and 150 ml glacial acetic acid were combined in a 250 ml flask and the suspension stirred at 57° C. To this mixture was added dropwise 30.9 g acetic anhydride over a period of 20 minutes at 47° C. The resulting solution was then stirred at room temperature for two hours, after which solvents were removed in vacuo to yield a white semi-solid. This material was suspended in 20 ml $H_2O$ and re-dried three times to yield a white solid, which was recrystallized from ether/acetone to yield 20.7 g of the product, N-acetyl-D,L-2-amino-5-methylhexanoic acid.

18 g of this material was taken up in 700 ml $H_2O$, and conc. $NH_4OH$ added to reach pH 7.2. The solution was heated to 36° C. and 11.0 mg Acylase I was added. After stirring for 18 hours, an additional 5 mg Acylase I was added and the solution stirred an additional 24 hours. The solution was then acidified with 18.0 ml acetic acid and filtered. Evaporation of the filtrate yielded the product, a white solid, L-2-amino-5-methyl hexanoic acid, (5.8 g, 83% yield).

Step 3: Synthesis of L-2-amino-5-methylhexanol

To 220 ml of 1.0 M $BH_3$ in tetrahydrofuran, chilled to 15° C. and under $N_2$ atmosphere, was added 8.0 g of L-2-amino-5-methylhexanoic acid in small portions over 30 minutes. The resulting solution was stirred at room temperature for 20 hours. The mixture was then chilled to −15° C. and 3 N NaOH was added dropwise over 2 hours until the vigorous evolution of gas subsided, after which 150 ml additional 3 N NaOH was added and the mixture stirred at room temperature for 20 hours. The resulting solution was then extracted with 3×450 ml portions of ether, and the combined ether fractions evaporated to dryness yielding 7.1 g of a pale yellow oil. This material was added to 50 ml 3 N NaOH and refluxed for two hours. Extraction of this mixture with 3×100 ml portions of ether and evaporation of solvents yielded 1.53 g of pure product, L-2-amino-5-methylhexanol (B.P. 96°–103° C./5 mm).

Step 4: Synthesis of N-(α-L-aspartyl)-L-1-hydroxymethyl-4-methylpentylamide 14.6 g N-carbobenzoxy-L-aspartic acid β-benzyl ester was suspended in 300 ml methylene dichloride and chilled in an ice-water bath. To the stirred suspension was added dropwise a slurry of 8.44 g dicyclohexylcarbodiimide in 25 ml methylene dichloride. The mixture was stirred for one hour at 5°–10° C. To this was added 4.13 g of L-2-amino-5-methylhexanol over 15 minutes while stirring at 5° C. The mixture was stirred for 60 hours, after which the mixture was filtered and the solvent was evaporated. The resulting residue from the evaporated filtrate were taken up in ether and filtered. The filtrate was evaporated to a solid which was taken up in 700 ml ether and washed successively with 2×150 ml portions each of 10% HCl, $H_2O$, 10% NaOH and saturated NaCl. The washed ether layer was dried over $MgSO_4$ and evaporated to yield 13.7 g N-carbobenzoxy-α-L-aspartyl-L-2-amino-5-methylhexanol, β-benzyl ester (71% yield).

This material was taken up in 150 ml acetic acid, to which 100 mg Pd on charcoal was added. The mixture was hydrogenated in a Parr apparatus at 50 psi $H_2$ to yield the crude product. The solvent was evaporated, affording a sticky yellow solid. This material was taken up in 18 ml acetic acid and further purified by HPLC on a preparative silica gel column using as solvent $CHCl_3$:methanol:water:acetic acid (64:30:4:2). Recrystallization from n-butanol/$H_2O$ (6:1) yielded 0.39 g of product, N-(α-L-aspartyl)-L-1-hydroxymethyl-4-methylpentylamide.

INDUSTRIAL APPLICABILITY

The sweetener agents of the present application can be used in many, varied preparations.

EXAMPLE I

The preparation of a typical sweetened orange soda is as follows:

A stock supply of bottler's syrup is prepared by mixing 5.5 ml. of a 50% aqueous citric acid solution with 150 ml. of water, dissolving 2 g. of N-(α-L-aspartyl)-L-1-hydroxymethyl-4-methylpentylamide in that solution, adding successively 7.02 ml. of the orange flavor base manufactured by A. E. Illes, Dallas, Texas, labeled FO-78, and 2.7 g. of sodium benzoate and diluting that mixture to 200 ml. with water. One oz. samples of the syrup so prepared are transferred to 6 oz. bottles and 110 ml. of cold tap water is added to each bottle. To each bottle, 42 ml. of cold charged bottling water (5 volumes carbon dioxide) is then added to achieve carbonation. Each bottle is capped and the contents mixed.

The bottled orange soda preparations possess a sweetness comparable to those containing a quantity of sucrose approximately 50 times that of the named aspartate amide.

Orange soda of similar sweetness intensity can be prepared using N-α-L-aspartyl derivatives wherein the L-amide moiety is:
1-hydroxymethyl-4,4-dimethylpentylamide,
1-hydroxymethyl-5-methylhexylamide,
1-hydroxymethylhexylamide,
1-hydroxymethyl-4-methylhexylamide,
1-hydroxymethyl-4,4-dimethylhexylamide,
1-hydroxymethylpentylamide, or
1-hydroxymethyl-5,5-dimethylhexylamide.

The sweetener compounds can also be used in various formulations for use in oral hygiene.

EXAMPLE II

A toothpaste composition is prepared by blending the following ingredients:

| Ingredient | Percent by weight |
| --- | --- |
| Calcium pyrophosphate* | 40.00 |
| Sorbitol (70% aqueous solution) | 20.40 |
| Glycerine | 10.20 |
| Sodium coconut monoglyceride sulphonate | 0.80 |
| Sodium carboxymethyl cellulose | 1.20 |
| Sodium coconut alkyl sulphate (20% active) | 2.30 |
| Sodium fluoride | 0.22 |
| Sweetener (N-α-L-aspartyl-L-1-hydroxymethyl-4,4-dimethyl-hexylamide) | 0.40 |
| Flavor | 0.90 |
| Green urea formaldehyde agglomerates | 0.65 |
| Water and minor ingredients | Balance |

*Standard dentifrice abrasive

The toothpaste of this Example is prepared in standard fashion by blending the ingredients until a smooth paste is secured and deaerating and tubing the product. The product possesses highly desirable sweetness, flavor and stability characteristics.

Toothpaste of similar sweetness intensity can be prepared using N-α-L-aspartyl derivatives wherein the L-amide moiety is:
1-hydroxymethyl-4,4-dimethylpentylamide,
1-hydroxymethyl-5-methylhexylamide,
1-hydroxymethylhexylamide,
1-hydroxymethyl-4-methylhexylamide,
1-hydroxymethyl-4,4-dimethylhexylamide,
1-hydroxymethylpentylamide, or
1-hydroxymethyl-5,5-dimethylhexylamide.

EXAMPLE III

A mouthwash is prepared by co-dissolving the following ingredients:

| Ingredient | Percent by Weight |
| --- | --- |
| Glycerine | 10.00 |
| Ethyl alcohol | 17.00 |
| Cetyl pyridinium chloride | 0.05 |
| Sorbitan monooleate polyoxyethylene | 0.13 |
| Flavor (Oil of Wintergreen) | 0.09 |
| Sweetening agent (L-aspartyl-L-1-hydroxymethyl-4-methyl-pentylamide) | 0.5 |
| Water and minor ingredients | Balance |

The above composition possesses highly desirable mouth-freshening characteristics and is desirably stable and sweet, with no noticeable bitter after-taste.

Mouthwash of similar sweetness intensity can be prepared using N-α-L-aspartyl derivatives wherein the L-amide moiety is:
1-hydroxymethyl-4,4-dimethylpentylamide,
1-hydroxymethyl-5-methylhexylamide,
1-hydroxymethylhexylamide,
1-hydroxymethyl-4-methylhexylamide,
1-hydroxymethyl-4,4-dimethylhexylamide,
1-hydroxymethylpentylamide, or
1-hydroxymethyl-5,5-dimethylhexylamide.

EXAMPLE IV

A gel dentifrice is prepared by conventional means having the following formulation:

| Ingredients | Percent by Weight |
| --- | --- |
| Silica xerogel | 12.00 |
| Silica aerogel | 5.00 |
| Hydroxyethyl cellulose | 1.50 |
| Glycerine | 34.76 |
| Stannous fluoride | 0.41 |
| Flavor (Wintergreen) | 0.95 |
| Color (FD & C Blue #1) | 0.03 |
| 21% sodium lauryl sulphate-79 glycerine mixture | 6.00 |
| Sweetener (N-α-L-aspartyl-L- | |

| Ingredients | Percent by Weight |
| --- | --- |
| 1-hydroxymethyl-5-methyl-hexylamide | 0.30 |
| Water and minor ingredients | Balance |

The above composition is prepared by blending and deaerating the listed ingredients in standard fasion. The product is a stable, effective, translucent dentifrice having desirable sweetness characteristics.

EXAMPLE V

A cough syrup is prepared by conventional means by using the sweeteners of the present invention to mask the bitter taste of the active ingredient, e.g., Pholcodine citrate syrup:

| Ingredients | Percent by Weight |
| --- | --- |
| Pholcodine | 8 mg |
| Citric acid | 80 mg |
| 90% Ethanol | 0.6 ml |
| Syrup (prepared by adding purified water to 13 g N-α-L-aspartyl-L-1-hydroxy-methyl-4-methylpentylamide to a total of 1000 g) | to 4 ml |

The composition is prepared by mixing the Pholcodine and the citric acid separately in 0.3 ml portions of the 90% ethanol, mixing the two portions of ethanol together, and combining the Pholcodine/citric acid/ethanol mixture with the syrup.

A dose of 2–4 ml administers an effective, non-bitter tasting, cough suppressing dose of Pholcodine without the use of the heavy sucrose syrups usually employed to mask the bitter taste of such products.

EXAMPLE VI

A chewing gum is prepared by replacing the sucrose normally added to chewing gum with the sweeteners of the instant invention. A gum base is prepared from:

| Ingredients | Weight in Grams |
| --- | --- |
| 60% latex | 18 |
| Hydrogenated rosin esters | 44 |
| Paracumarine resin | 7.5 |
| Candellila wax | 6 |
| Glyceryl tristearate | 2.5 |
| Ethyl cellulose | 2 |
| Calcium carbonate | 20 |

The aforesaid gum base is used with the sweeteners of this invention to prepare a chewing gum having a greatly reduced sucrose content, hence less cariogenic potential, while maintaining a desirable sweetness level:

| Ingredients | Percent by Weight |
| --- | --- |
| Gum base | 68 |
| N-(α-L-aspartyl)-L-1-hydroxymethyl-4-methyl pentylamide | 15 |
| Corn syrup | 16 |
| Flavor | 1 |

Chewing gum of similar sweetness intensity can be prepared using N-α-L-aspartyl derivatives wherein the L-amide moiety is:
1-hydroxymethyl-4,4-dimethylpentylamide,
1-hydroxymethyl-5-methylhexylamide,
1-hydroxymethylhexylamide,
1-hydroxymethyl-4-methylhexylamide,
1-hydroxymethyl-4,4-dimethylhexylamide,
1-hydroxymethylpentylamide, or
1-hydroxymethyl-5,5-dimethylhexylamide.

EXAMPLE VII

Sweetening compositions for addition to foods and beverages (e.g., coffee and tea) to enable edible materials to be sweetened to suit individual tastes can be prepared in liquid or solid form. A liquid sweetener can be prepared using from 5–10% sweetener, 0.1% benzoic acid and 0.05% methyl paraben in purified water. Sweetening tablets, for addition to coffee, for example, can be prepared using 20–80 mg of sweetener per tablet and standard excipients such as sodium bicarbonate, sodium benzoate, soda ash, sodium citrate, tartaric acid, and sodium gluconate in standard tabletting procedures. The following are representative.

| Ingredients | Amount |
| --- | --- |
| Tablet A | |
| Starch | 120 mg |
| N-(α-L-aspartyl)-L-1-hydroxy-methyl-4-methylpentylamide | 60 mg |
| Magnesium Stearate | 5 mg |
| Tablet B | |
| Carboxymethylcellulose | 80 mg |
| N-(α-L-aspartyl)-1-hydroxy-methyl-5-methylhexylamide | 80 mg |
| Mg Stearate | 3 mg |
| Tablet C | |
| Lactose | 10 mg |
| Starch | 100 mg |
| N-(α-L-aspartyl)-1-hydroxy-methyl-4,4-dimethylpentylamide | 70 mg |
| Magnesium Stearate | 3 mg |

As can be seen from the foregoing, compositions intended for oral ingestion can be sweetened by using at least about 0.01 mg, usually about 20 mg to about 1500 mg, of the compounds of their invention, per 100 g of composition.

What is claimed is:

1. A compound of the formula:

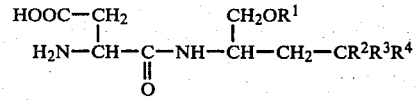

wherein said compound is in the L,L configuration; and wherein $R^1 = H$, $R^2 = H$ or $CH_3$; $R^3 = H$ or $CH_3$; and $R^4 = CH_3$, $C_2H_5$, i—$C_3H_7$ or t—$C_4H_9$; except that where $R^4$ is i—$C_3H_7$ or t—$C_4H_9$, $R^2$ and $R^3$ are H; and toxicologically acceptable salts thereof.

2. The sodium, potassium, calcium, ammonium or hydrochloride salt of a compound according to claim 1.

3. A compound according to claim 2 wherein $R^2$ is H and $R^3$ and $R^4$ are —$CH_3$.

4. N-(α-L-aspartyl)-L-1-hydroxymethyl-4-methylpentylamide and toxicologically acceptable salts thereof.

5. A composition of matter for oral ingestion comprising an effective sweetening amount of a compound according to claim 1 and a carrier.

6. A food, beverage, mouthwash, or dentifrice composition according to claim 5.

7. A composition according to claim 6 wherein said compound is N-(α-L-aspartyl)-L-1-hydroxymethyl-4-methylpentylamide.

8. A process for sweetening compositions intended for oral ingestion, comprising adding to said composition to be ingested orally an effective sweetening amount of a compound according to claim 1.

* * * * *